United States Patent

Axelsson et al.

[11] Patent Number: 5,904,825
[45] Date of Patent: May 18, 1999

[54] GEL ELECTROPHORESIS APPARATUS

[75] Inventors: Urban Jonsson Axelsson, Kista; Göran Andersson, Enköping; Stefan Sowa, Uppsala, all of Sweden

[73] Assignee: Pharmacia Biotech AB, Uppsala, Sweden

[21] Appl. No.: 08/776,247
[22] PCT Filed: Jul. 21, 1995
[86] PCT No.: PCT/SE95/00880
    § 371 Date: Mar. 12, 1997
    § 102(e) Date: Mar. 12, 1997
[87] PCT Pub. No.: WO96/04549
    PCT Pub. Date: Feb. 15, 1996

[30] Foreign Application Priority Data

Jul. 29, 1994 [SE] Sweden .................................. 9402606

[51] Int. Cl.⁶ .................................................. G01N 27/26
[52] U.S. Cl. .......................................... 204/616; 204/618
[58] Field of Search ................................... 204/456, 466, 204/467, 616, 618, 617

[56] References Cited

U.S. PATENT DOCUMENTS

| | | | |
|---|---|---|---|
| 3,129,158 | 4/1964 | Raymond et al. | 204/467 |
| 4,315,812 | 2/1982 | Karlson | 204/647 |
| 4,747,919 | 5/1988 | Anderson | 204/455 |

FOREIGN PATENT DOCUMENTS

| | | |
|---|---|---|
| 0224194 | 6/1987 | European Pat. Off. |
| 0339975 | 11/1989 | European Pat. Off. |
| 339975 A2 | 11/1989 | European Pat. Off. |
| 9210744 | 6/1992 | WIPO |

*Primary Examiner*—William H. Beisner
*Assistant Examiner*—Alex Noguerola
*Attorney, Agent, or Firm*—Birch, Stewart, Kolasch & Birch, LLP

[57] ABSTRACT

A gel electrophoresis apparatus for receiving a gel cassette is adapted to receive the gel cassette inclined to such an extent that the upper edge of the gel can be seen at an angle from above through the liquid surface in the upper buffer container.

15 Claims, 1 Drawing Sheet

GEL ELECTROPHORESIS APPARATUS

TECHNICAL FIELD

The present invention relates to an arrangement in a gel electrophoresis apparatus for receiving a gel package, usually called a gel cassette.

BACKGROUND OF THE INVENTION

In gel electrophoresis apparatuses known so far, the gels are received either vertically or horizontally, i.e. the gels either stand upright in the gel electrophoresis apparatuses or lie horizontally in the gel electrophoresis apparatuses. Usually, the necessary electrophoresis buffer is provided from two connecting liquid tanks or buffer containers, thus for a vertical gel an upper and a lower buffer container.

A disadvantage of receiving a gel in a gel cassette vertically in a gel electrophoresis apparatus is that the working position for the person who loads the gel with samples is very uncomfortable in that the refraction of light in the glass plates of the gel cassette makes it very difficult to clearly see the gel edge without placing one's eyes closely by the gel cassette at the same time as the pipette with which the wells are loaded, has to be brought up above eye-level in order for the samples to be applied in a correct manner into the wells without the pipette tip contacting and damaging the gel. Neither is it possible to instead look at the gel edge straight from above through the liquid surface in the upper buffer container to which the gel cassette is connected, since the vertical position of the pipette tip in relation to the gel edge can then not be determined.

The disadvantage of horizontally mounted gels is that present systems for loading of samples restrict the resolution which is the reason why horizontal systems cannot be used when a high resolution is required.

EP-A-339 975 discloses a gel electrophoresis apparatus where the gel cassette is inclined between 5° and 10° relative to the vertical plane. The purpose of the inclination is to facilitate the handling of the apparatus in that the inclination prevents the gel cassette from tipping when it is being clamped to the electrophoresis apparatus. The above difficulty of clearly seeing the gel edge is neither mentioned nor overcome by means of this inclination.

SUMMARY OF THE INVENTION

The object of the present invention is to bring about a gel electrophoresis apparatus at which the working position for a user, primarily the person who loads the gel with samples, will be much more comfortable in comparison with the working position at gel electrophoresis apparatuses with vertical gel known so far.

This is attained, mainly, in that the gel electrophoresis apparatus is adapted to receive the gel cassette inclined to such an extent that the upper edge of the gel can be seen through the liquid surface of the upper buffer container.

Hereby, the working position for the person who loads the gel will be much improved in comparison with the conditions at a gel in an upright position in that both the pipette tip and the gel edge will be clearly visible at an angle from above through the liquid surface in the upper buffer container, and, consequently, the pipette does not have to be brought above eye-level in connection with the loading of the samples.

The necessary inclination of the gel cassette in relation to the vertical plane for this to be achieved is normally about 15° or greater, e.g. in the range of 15° to 30°. With a smaller inclination, such as in the above-mentioned EP-A-339 975, or with a completely vertical gel, light refraction phenomena in the liquid surface makes it impossible to see and estimate the distance to the upper edge of the gel through the liquid surface.

In addition to the working position thus being better when one can look from above during the sample application, several further advantages are attained, such as that the upper liquid tank (buffer container) can be made of a non-transparent material and can be mounted to the operator side of the gel package which leads to greater freedom in the construction.

BRIEF DESCRIPTION OF THE DRAWING

The present invention will become more fully understood from the detailed description given hereinbelow and the accompanying drawing which is given by way of illustration only, and thus is not limitative of the present invention, and wherein:

The figure is a schematic perspective view of an embodiment of a gel electrophoresis apparatus according to the invention.

DESCRIPTION OF A PREFERRED EMBODIMENT

Figure 1:
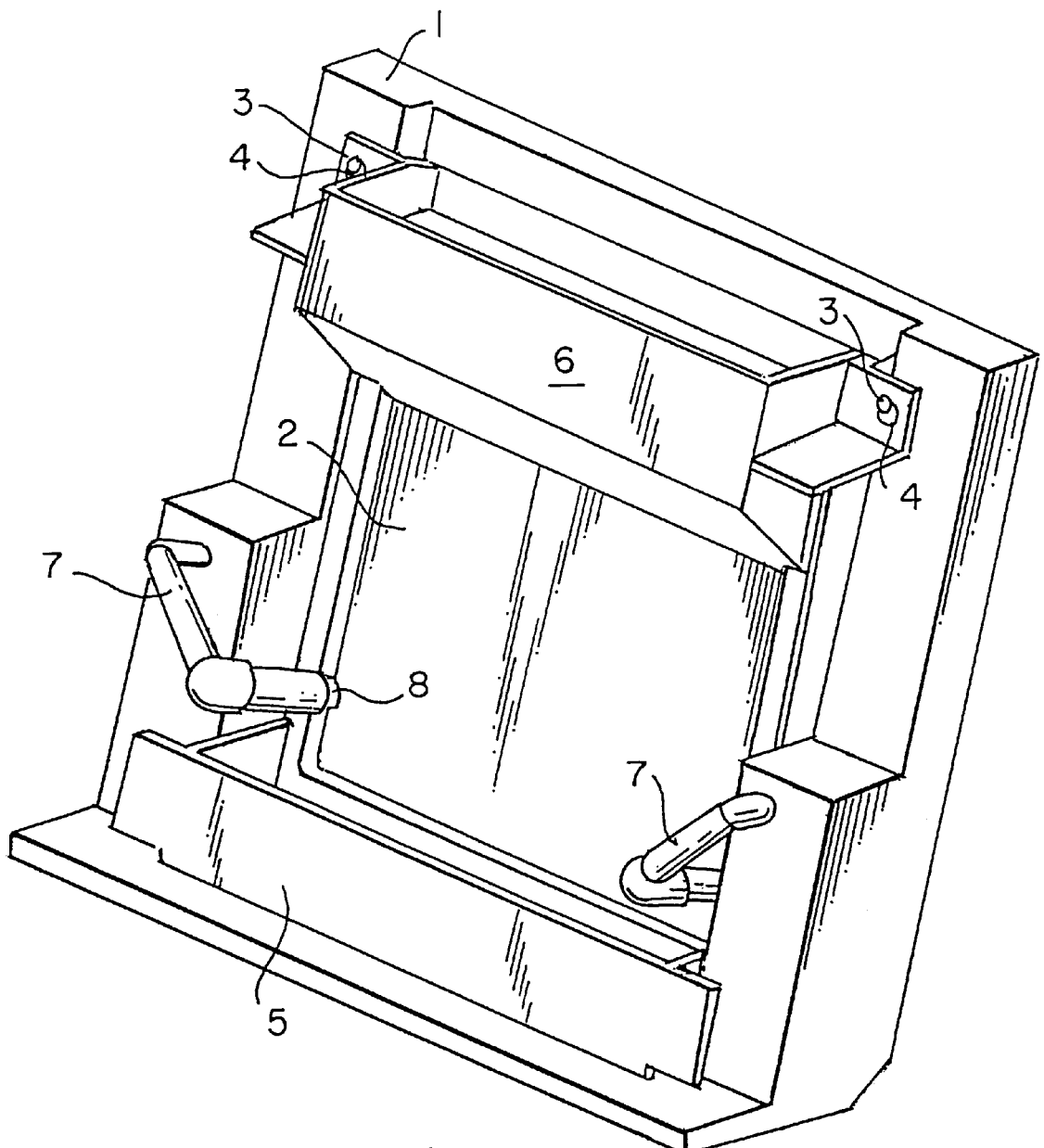

The gel electrophoresis apparatus shown comprises a stand 1 for receiving and supporting a gel cassette 2. The stand 1 of the gel electrophoresis apparatus receives the gel cassette 2 with an upper part of the gel cassette 2 leaning away from a user relative to a vertical plane. The stand 1 supports the gel cassette 2 at an inclined angle of about 15° or greater with respect to a vertical plane such that the upper part of the gel cassette 2 leans away from a user. The inclination of the gel cassette 2 is preferably in the range of 15° to 30° with respect to the vertical plane.

The stand 1 is provided with a pair of pins 3 which cooperate with recesses or openings 4 in the gel cassette 2 so that the gel cassette 2 can be hung on the pins 3 of the stand 1. As shown in FIG. 1, when the gel cassette 2 is hung on the pins 3 of the stand 1, the gel cassette 2 rests against the stand 1. Thus, the stand 1 supports the gel cassette 2. Further, as set forth above, the stand 1 supports the gel cassette 2 such that the upper part of the gel cassette 2 leans away from a user at an inclined angle preferably in the range of 15° to 30°.

In this connection, it should be noted that, as an alternative, the gel cassette could lean towards a user.

In a manner known per se, the gel cassette 2 comprises two glass plates (not shown) between which a gel (not shown), e.g. for nucleic acid separation, is cast.

The lower part of the gel cassette 2 is, in a manner known per se, received in a lower buffer container 5, while an upper buffer container 6, necessary for an electrophoresis run, in the illustrated case in accordance with the invention is fixed to that glass plate of the gel cassette 2 which faces away, or is spaced further away, from the stand 1.

To keep the gel cassette 2 in a fixed position against the stand 1, two schematically illustrated brackets 7 are provided, which preferably are spring-loaded in a manner not shown more in detail for biasing the brackets 7 against the gel cassette 2, to thereby bias the gel cassette 2 against the stand 1.

In the embodiment shown, the gel cassette is temperature regulated in that a further plate is provided on the glass plate of the gel cassette 2 which faces away from the stand 1, for forming an interspace between these plates, through which interspace temperature regulated water circulates from a schematically shown inlet 8 to an outlet which is not shown on the drawing.

According to the invention, the spring-loaded brackets 7 include tubes to be connected to the inlet means 8 and outlet means (not shown) of the gel cassette 2.

Electrodes (not shown), necessary for carrying out an electrophoresis run, are in accordance with the invention provided with brackets (not shown) to make it possible to hang the electrodes in the upper and lower buffer containers 6 and 5, respectively.

To protect the respective electrode and prevent the buffer liquid in the buffer containers 5 and 6 from being contaminated, each buffer container 5 and 6 is provided with a lid (not shown). In accordance with the invention, the respective electrode may be integrated in the respective lid. Moreover, the lids reduce the evaporation of buffer liquid from the buffer containers during a run which is of great advantage since, without lids, the evaporation can be so extensive that the separation result deteriorates.

As should be understood, the working position for a person who loads the gel with samples will be considerably improved with an inclined gel cassette as above in comparison with an upright standing gel cassette, mainly since the person who loads the samples will be able to clearly see the gel edge through the liquid surface in the upper buffer container due to the refraction of light in the buffer liquid surface.

The invention is, of course, not restricted to the embodiment described above and shown in the drawing, but many changes and modifications can be made within the scope of the general inventive concept as defined in the following claims.

We claim:

1. A gel cassette electrophoresis apparatus comprising:

a stand for receiving a gel cassette therein, said stand supporting said gel cassette at an inclined angle of about 15° or greater with respect to a vertical plane passing through said stand; and an upper buffer container located on an upper portion of said stand for receiving a buffer liquid therein, wherein an upper edge of a gel located in said gel cassette is visible through a liquid surface of said buffer liquid in said upper buffer container due to said inclined angle of said gel cassette.

2. The gel cassette electrophoresis apparatus according to claim 1, further comprising:

at least one suspension pin located on said stand for cooperating with a recess provided on said gel cassette; and at least one bracket located on said stand, said bracket including a spring for biasing said bracket against said gel cassette, to thereby bias the gel cassette against said inclined support surface.

3. The gel cassette electrophoresis apparatus according to claim 1, wherein the inclination of the gel cassette is in the range of 15° to 30° with respect to the vertical plane.

4. The gel cassette electrophoresis apparatus according to claim 1, wherein the gel cassette comprises first and second glass plates, the first glass plate being spaced apart from said second glass plate, and wherein the upper buffer container of the gel electrophoresis apparatus is fixed to the first glass plate.

5. The gel cassette electrophoresis apparatus according to claim 1, further comprising a lower buffer container for receiving the lower part of the gel cassette, wherein electrodes, necessary for carrying out a gel electrophoresis run, are provided with brackets for hanging the electrodes in the upper and lower buffer containers, respectively.

6. The gel cassette electrophoresis apparatus according to claim 5, wherein the respective electrode is integrated in a lid designed for the respective buffer container.

7. The gel cassette electrophoresis apparatus according to claim 1, wherein the gel electrophoresis apparatus receives the gel cassette with its upper part leaning away from a vertical plane extending through a lower part of said gel cassette.

8. The gel cassette electrophoresis apparatus according to claim 1, wherein brackets are provided to keep the gel cassette against said stand.

9. The gel cassette electrophoresis apparatus according to claim 8, wherein the gel cassette comprises inlet and outlet means for water to temperature-regulate the gel cassette by circulation of said water, and wherein said brackets include tubes to be connected to said inlet and outlet means of the gel cassette.

10. The gel cassette electrophoresis apparatus according to claim 8, wherein said brackets are spring-loaded.

11. The gel cassette electrophoresis apparatus according to claim 10, wherein the gel cassette comprises inlet and outlet means for water to temperature-regulate the gel cassette by circulation of said water, and wherein said brackets include tubes to be connected to said inlet and outlet means of the gel cassette.

12. The gel-cassette electrophoresis apparatus according to claim 1, wherein said stand includes suspension pins for cooperation with recesses provided on the gel cassette for hanging the gel cassette on said stand.

13. The gel cassette electrophoresis apparatus according to claim 12, wherein brackets are provided to keep the gel cassette against said stand.

14. The gel cassette electrophoresis apparatus according to claim 13, wherein said brackets are spring-loaded.

15. The gel cassette electrophoresis apparatus according to claim 14, wherein the gel cassette comprises inlet and outlet means for water to temperature-regulate the gel cassette by circulation of said water, and wherein said brackets include tubes to be connected to the inlet and outlet means of said gel cassette.

* * * * *